(12) United States Patent
Cummins et al.

(10) Patent No.: US 10,660,677 B2
(45) Date of Patent: May 26, 2020

(54) EXPANDABLE BONE PLATE ASSEMBLIES

(71) Applicant: ZAVATION MEDICAL PRODUCTS LLC, Flowood, MS (US)

(72) Inventors: John Franklin Cummins, Kosciusko, MS (US); John Lawrence Walker, Madison, MS (US); Eric Graham, Ocean Springs, MS (US)

(73) Assignee: ZAVATION MEDICAL PRODUCTS, LLC, Flowood, MS (US)

( * ) Notice: Subject to any disclaimer, the term of this patent is extended or adjusted under 35 U.S.C. 154(b) by 246 days.

(21) Appl. No.: 15/927,586

(22) Filed: Mar. 21, 2018

(65) Prior Publication Data
US 2018/0271570 A1  Sep. 27, 2018

Related U.S. Application Data (60) Provisional application No. 62/512,986, filed on May 31, 2017, provisional application No. 62/474,768, filed on Mar. 22, 2017.

(51) Int. Cl.
*A61B 17/80* (2006.01)
*A61B 17/70* (2006.01)

(52) U.S. Cl.
CPC ...... *A61B 17/8023* (2013.01); *A61B 17/7059* (2013.01); *A61B 17/8042* (2013.01)

(58) Field of Classification Search
CPC ............ A61B 17/8023; A61B 17/7059; A61B 17/8042
See application file for complete search history.

(56) References Cited

U.S. PATENT DOCUMENTS

| | | | |
|---|---|---|---|
| 6,402,756 B1 | 6/2002 | Ralph et al. | |
| 7,118,573 B2 * | 10/2006 | Michelson | A61B 17/7059 606/71 |
| 7,186,256 B2 * | 3/2007 | Michelson | A61B 17/7059 606/279 |
| 9,101,422 B2 | 8/2015 | Freid et al. | |
| 2002/0183757 A1 * | 12/2002 | Michelson | A61B 17/7059 606/71 |
| 2004/0210217 A1 * | 10/2004 | Baynham | A61B 17/686 606/295 |
| 2005/0010227 A1 * | 1/2005 | Paul | A61B 17/7059 606/71 |
| 2012/0083846 A1 | 4/2012 | Wallenstein et al. | |
| 2012/0158059 A1 | 6/2012 | Freid et al. | |

* cited by examiner

*Primary Examiner* — Christian A Sevilla
(74) *Attorney, Agent, or Firm* — Ronald A. Rudder; Olive Law Group, PLLC (57) ABSTRACT

An expandable bone plate assembly is provided having a top plate portion and a bottom plate portion. A back side of the top plate portion has a longitudinally extending blind slot. A transversely extending counterbore extends through front back sides of the top plate portion. A transversely extending bore extends through the front and back sides of the bottom plate portion. The bone plate assembly also includes a pin with a pin head and a pin shaft depending from the pin head. The pin shaft is disposed within the transversely extending bore of the bottom plate portion and has an outer diameter greater than the minor diameter of the transversely extending bore. The pin head is disposed against the longitudinally extending blind slot of the top plate portion.

12 Claims, 10 Drawing Sheets

EXPANDABLE BONE PLATE ASSEMBLIES

CROSS-REFERENCE TO RELATED APPLICATIONS

The present application claims priority to U.S. Provisional Application. No. 62/512,986 filed on May 31, 2017 and U.S. Patent Application No. 62/474,768 filed on Mar. 22, 2017, the entirety of both applications incorporated by reference herein.

TECHNICAL FIELD

The present disclosure relates to expandable bone plate assemblies.

BACKGROUND

Internal fixation devices, such as plates, pins, rods, wires and screws, are often used to stabilize and join bones. For example, a bone plate can be used to facilitate healing of bone fractures or to fuse adjacent vertebral bodies of a patient's spinal column. The plate is placed against adjacent bone tissue and screws are inserted through screw holes of the plate into the adjacent bone tissue to anchor the plate into proper position.

Many bone plates are of fixed height or expandable. Fixed bone plates are manufactured in various heights so that one plate can be selected to best fit adjacent bone tissue. Alternatively, an expandable bone plate has an adjustable height to maintain spacing of the vertebrae above and below the removed vertebral or disc material. Both types of bone plates have limitations and problems. Fixed bone plates have good structural integrity but can be cumbersome to place. Further, the fixed bone plate must be exactly the correct height. If the bone plate is too large, it can cause over distraction to the vertebral bodies or damage the vertebral body above and below the bone plate. If the bone plate is too small, it can displace out of position. Expandable bone plates are much easier to correctly size and place. However, the mechanical mechanism used to expand the bone plate may fail after implantation. The interconnection between components of an expandable bone plate should be secure enough such that the bone plate does not disassemble prior to or after implantation.

SUMMARY

The present disclosure relates to expandable bone plate assemblies. In an embodiment, an expandable bone plate assembly comprises a top plate portion and a bottom plate portion. The top plate portion has a front side and a back side. The back side comprises a longitudinally extending blind slot. A transversely extending counterbore extends through the front and back sides of the top plate portion. One or more bone screw holes extend through the front and back sides of the top plate portion. The bottom plate portion of the expandable bone plate assembly also comprises a front side and a back side. A transversely extending bore extends through the front and back sides of the bottom plate portion. One or more bone screw holes extend through the front and back sides of the bottom plate portion. The bone plate assembly also includes a pin comprising a pin head and a pin shaft depending from the pin head. The pin shaft is disposed within the transversely extending bore of the bottom plate portion and has an outer diameter greater than the minor diameter of the transversely extending bore. The pin head is disposed against the longitudinally extending blind slot of the top plate portion. The expandable bone plate assembly also includes a lock screw disposed within the transversely extending counterbore of the top plate portion.

DETAILED DESCRIPTION

Figure 1:
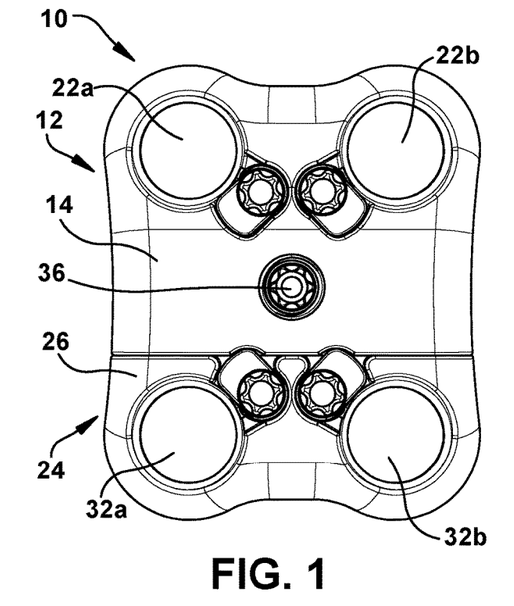
FIG. 1 is a front view of an expandable bone plate assembly according to an embodiment of the present disclosure.
Figure 2:
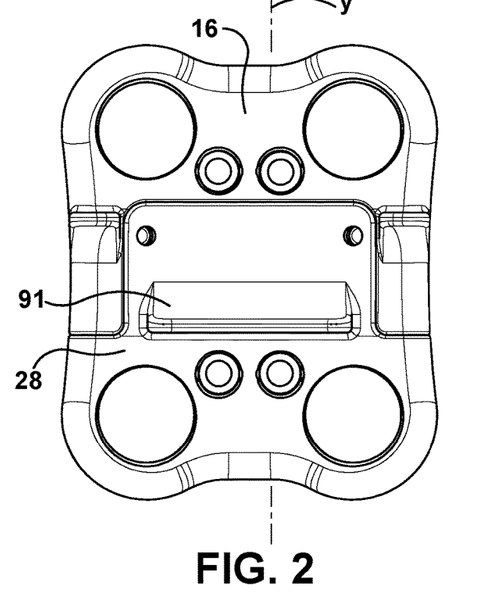
FIG. 2 is a back view of an expandable bone plate assembly according to an embodiment of the present disclosure.
Figure 7:
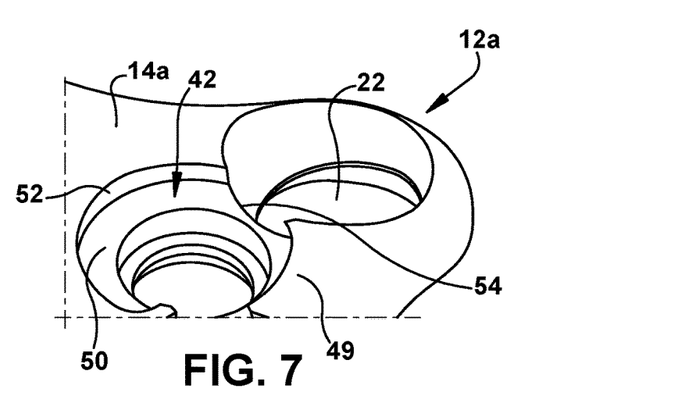
FIG. 7 is a partial perspective view of a top plate portion prior to full manufacturing and assembly of an expandable bone plate assembly according to an embodiment of the present disclosure.

The disclosure refers to the terms "top," "bottom," "front," and "back" with respect to certain components. These terms are used with respect to the orientation of an expandable bone plate assembly as illustrated in FIGS. 1 and 2. The disclosure also refers to the terms "left" and "right" with respect to certain components. These terms are used with respect to the orientation of an expandable bone plate assembly as illustrated in FIG. 1. The disclosure also refers to the term "lower" with respect to certain components. This term is used with respect to the orientation of a top plate portion as illustrated in FIG. 7. Further, as used herein with respect to a described element, the terms "a," "an," and "the" include at least one or more of the described element unless otherwise indicated. Further, the term "or" refers to "and/or" including combinations thereof unless otherwise indicated. In addition, the term "plurality" as used with respect to an element refers to more than one of the elements. In addition, it will be understood that when an element is referred to as being "over," "on," "attached" to, "connected" to, "coupled" to, "in fluid communication with," another element, it can be directly over, on, attached to, connected to, coupled to, in fluid communication with the other element or intervening elements may also be present. In contrast, when an element is referred to as being, for example, "directly over," "directly on," "directly attached" to, "directly connected" to, "directly coupled" to, or in direct fluid communication with another element, there are no intervening elements present.

Figure 18:
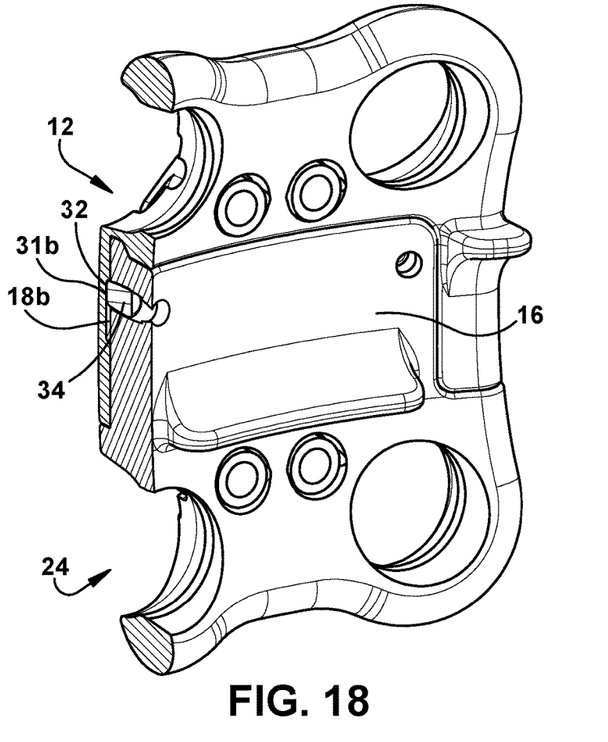
FIG. 18 is a partial cut-away view of an expandable bone plate assembly according to an embodiment of the present disclosure.

The present disclosure relates to expandable bone plate assemblies. Referring to FIGS. 1 and 2, in an embodiment, an expandable bone plate assembly 10 comprises a top plate portion 12 having a front side 14 and a back side 16. As illustrated in FIG. 18, back side 16 comprises a longitudinally extending blind slot 18. In certain embodiments, back side 16 comprises a left longitudinally extending blind slot and a right longitudinally extending blind slot. The length of longitudinally extending blind slot 18 determines the maximum height the expandable bone plate assembly can be expanded as described in more detail below. Top plate portion 12 also comprises a transversely extending counterbore 20 extending through the front and back sides 14 and 16 of the top plate portion 12. Transversely extending counter bore 20 does not necessarily extend at a right angle to the long axis Y of expandable bone plate assembly 10. Rather, transversely extending bore 20 extends along a plane different than the plane along which Y axis extends. Top plate portion 12 further includes a bone screw hole 22 extending through the front and back sides 14 and 16 of the top plate portion 12. Although the figures illustrate the top plate portion as having two bone screw holes, the top plate portion can have only one bone screw hole or a plurality of bone screw holes. In certain embodiments as illustrated in FIG. 3, the back side of top plate portion 12 comprises a longitudinally extending groove 38, such as a left longitudinally extending groove 38a and a right longitudinally extending groove 38b that is configured to accept a bottom plate portion of the plate assembly as described below.

Figure 5:
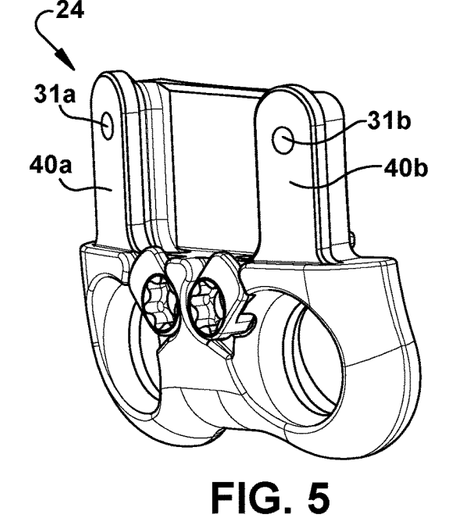
FIG. 5 is a perspective view of a bottom plate portion of an expandable bone plate assembly according to an embodiment of the present disclosure.

Expandable bone plate assembly 10 further comprises a bottom plate portion 24 comprising a front side 26, a back side 28, a transversely extending bore 30 extending through the front and back sides 26 and 28 of bottom plate portion 24 and a bone screw hole 32 extending through front and back sides 26 and 28 of bottom plate portion 24. The transversely extending bore can be a counterbore. The transversely extending bore does not necessarily extend at a right angle to the long axis Y of bone plate assembly 10. Rather, the transversely extending bore extends along a plane different than the plane along which Y axis extends. Although the figures illustrate two transversely extending bores in FIG. 6, a left transversely extending bore 30a and a right transversely extending bore 30b, the bottom plate portion can include only one transversely extending bore or a plurality of transversely extending bores. Similarly, although the figures illustrate the bottom plate portion as having two bone screw holes, the bottom plate portion can have only one bone screw hole or a plurality of bone screw holes. As illustrated in FIG. 5, the front side of the bottom plate portion can comprise a longitudinally extending tab 40, such as left longitudinally extending tab 40a and a right longitudinally extending tab 40b that is disposed in the respective left and right longitudinally extending grooves 38a and 38b of the back side of the top plate portion.

Figures 3, 4:
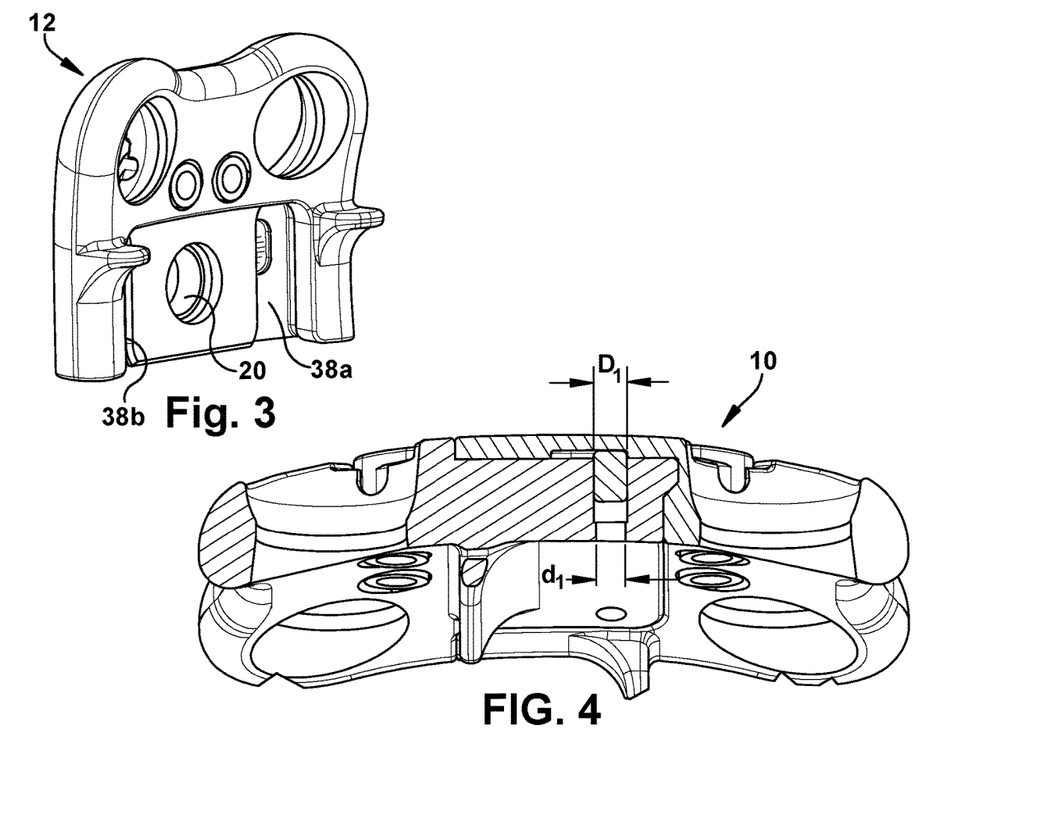
FIG. 3 is a side perspective view of a top plate portion of an expandable bone plate assembly according to an embodiment of the present disclosure.
FIG. 4 is a side partial cross-sectional view of an expandable bone plate assembly according to an embodiment of the present disclosure.
Figure 6:
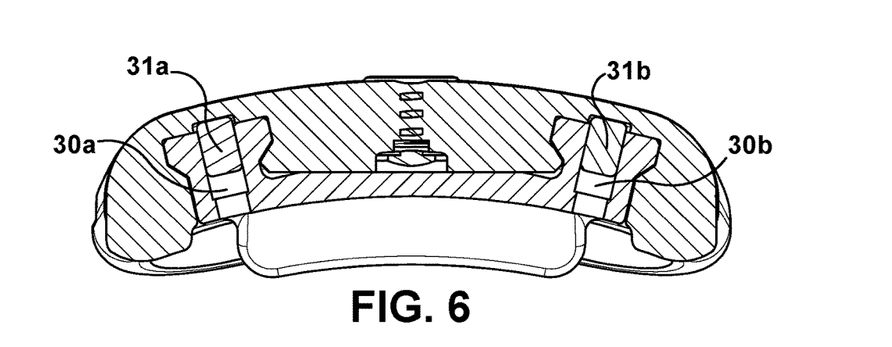
FIG. 6 is a side partial cross sectional view of an expandable bone plate assembly according to an embodiment of the present disclosure.

Referring to FIGS. 4, 6 and 18, bone plate assembly 10 further includes a pin 31 comprising a pin head 32 and a pin shaft 34 depending from pin head 32. Pin shaft 34 is disposed within transversely extending bore 30 of bottom plate portion 24 and has an outer diameter D1 greater than the minor diameter d1 of transversely extending bore 30. Pin head 32 is disposed against longitudinally extending blind slot 18 of top plate portion 12 as illustrated in FIG. 18. The number of pins in the bone plate assembly corresponds to the number of transversely extending bores of the bottom plate portion. Although the figures illustrate the expandable bone plate assembly as having a left pin 30a and a right pin 30b, the plate assembly can have only one pin or a plurality of pins. In embodiments where the transversely extending bore of the bottom plate portion is a counterbore, the pin head can comprise a flange that is disposed against the longitudinally extending blind slot of the top plate portion as described in detail in U.S. Patent Application No. 62/502,844 entitled: "Expandable Spinal Cage Assemblies for Supporting Bone Structures," filed on May 8, 2017, which is incorporated by reference in its entirety herein.

Bone plate assembly further comprises a lock screw 36 disposed within transversely extending counterbore 20 of top plate portion 12.

An advantage of such an expandable bone plate assembly is that the smaller components of the assembly such as the pin and lock screw are retained once the bone plate is assembled after manufacturing. This minimizes the risk of the expandable bone plate assembly coming apart after manufacturing (e.g. during shipping) and during and after implantation in a patient.

Figure 8:
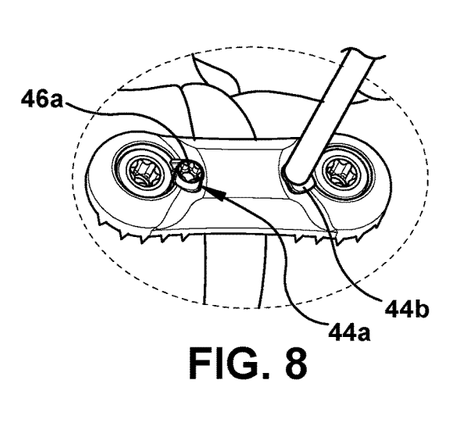
FIG. 8 is a perspective view illustrating bone screw locks being activated during a step of implanting an expandable bone plate assembly on vertebrae according to an embodiment of the present disclosure.
Figure 9:
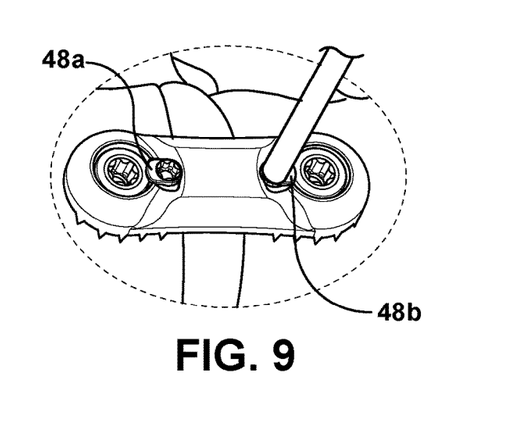
FIG. 9 is a perspective view illustrating bone screw locks being activated during a step of implanting an expandable bone plate assembly on vertebrae according to an embodiment of the present disclosure.

Bone plate assemblies can also include bone screw locks to prevent or minimize bone screws from backing out of the bone plate assemblies. For example, as illustrated in FIG. 7, a bone plate can comprise a recess 42 in fluid communication with a bone screw hole 22 of a top plate portion 12A. As shown in FIGS. 8 and 9, a rotatable bone screw lock 44 is mounted in the recess of top plate portion 12A and has a lock head 46 including a laterally extending flange 48, wherein in a locked position, a part of the laterally extending flange is within the bone screw hole of the top plate portion 45 as illustrated in FIG. 9.

Referring back to FIG. 7, recess 42 can be defined by a retention portion 49 of the front side 14A of top plate portion 12A, a lower surface 50 of top plate portion 12A, and a discontinuous wall 52 comprising a gap 54 in fluid communication with bone screw hole 22 of top plate portion 12A. In such an embodiment, the laterally extending flange of the bone screw lock has an outer edge that is below the front side of the top plate portion. In a locked position, a part of the laterally extending flange is within the gap 54 and another part of the lock head 46 is covered by retention portion 49 of top plate portion 12A. Such an embodiment of a bone screw lock is disclosed in U.S. Patent Application No. 62/474,768, entitled "Internal Fixation Device with Rotatable Screw Locks" filed on Mar. 22, 2017, which is incorporated by reference in its entirety herein. As illustrated in FIG. 1, the bone plate assembly can comprise a plurality of bone screw locks that correspond to the number of bone screw holes of the top plate portion and the bottom plate portion. Alternatively, a single bone screw lock can be used for more than one bone screw hole as illustrated and disclosed in U.S. Patent Application No. 62/474,768.

Figure 10A:
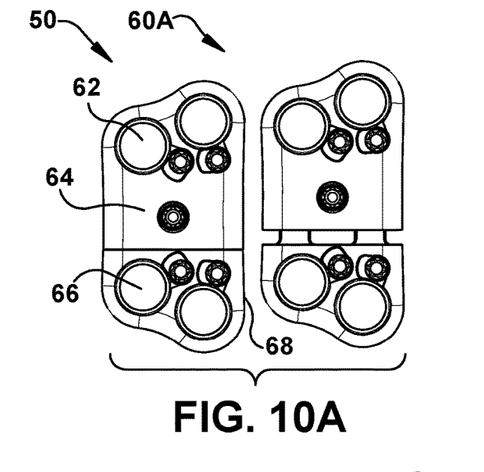
FIGS. 10A-10C are front views of a kit including expandable lateral bone plate assemblies according to an embodiment of a present invention illustrating such assemblies in a non-expanded position and a fully expanded position.
Figure 10B:
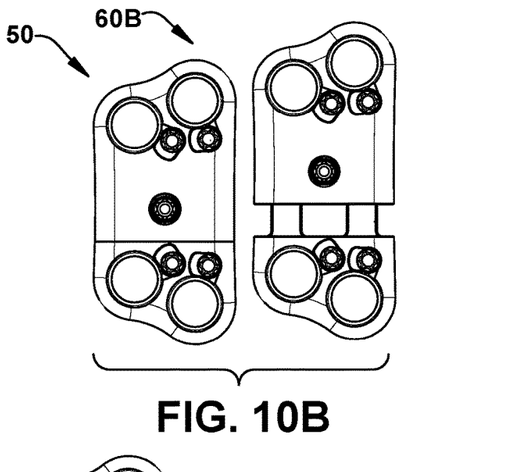
Figure 10C:
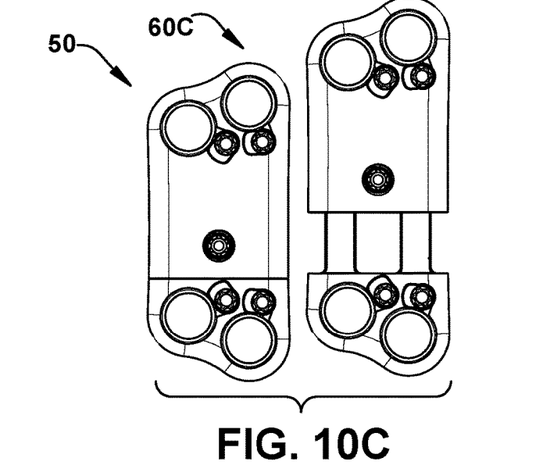
Figure 11:
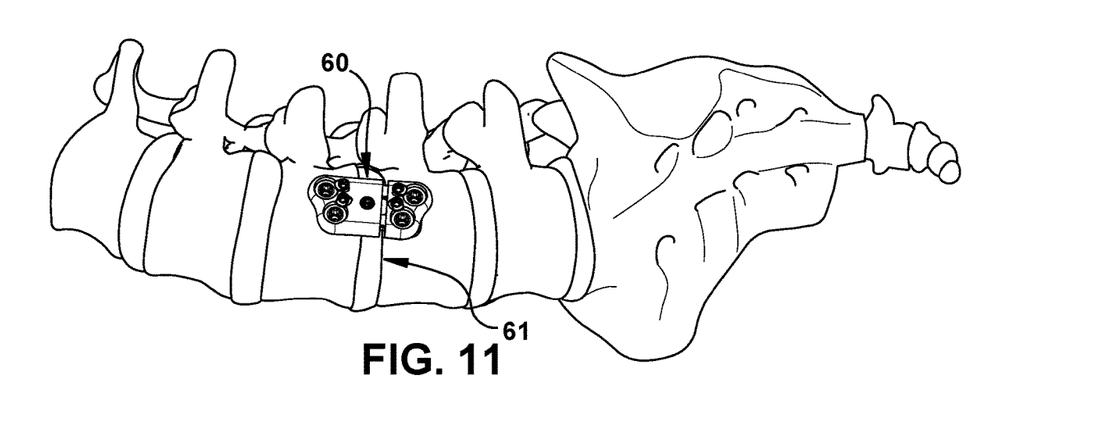
FIG. 11 is a perspective view of an expandable lateral bone plate assembly implanted on a lateral portion of vertebrae.

An expandable bone plate assembly can be part of a kit including expandable bone assemblies of different sizes. For example, kit 50 can include a plurality of expandable bone plate assemblies ranging in height in a fully expanded position. For example, referring to FIGS. 10A-10C, kit 50 can include three expandable lateral bone plate assemblies 60 ranging in size from approximately 25 millimeters (mm) to approximately 40 mm in a fully expanded position as measured from the center of the left screw hole 62 of top plate portion 64 to the center of left screw hole 66 of bottom plate portion 68. For example, expandable lateral bone plate assembly 60A schematically illustrated in FIG. 10A can range in height from approximately 22 mm in a non-expanded position to approximately 25 mm in a fully expanded position. Expandable lateral bone plate assembly 60B schematically depicted in FIG. 10B can range in height from approximately 25 mm in a non-expanded position to approximately 30 mm in a fully expanded position. Expandable lateral bone plate assembly 60C schematically illustrated in FIG. IOC can range in height from approximately 30 mm in a non-expanded position to approximately 44 mm in a fully expanded position. In certain embodiments, each expandable lateral bone plate assembly 60 includes four bone screw holes, four bone screw locks, is approximately 5 mm thick and is approximately 22 mm wide. Kit 50 can include different quantities of components of an expandable lateral bone plate assembly, different quantities of expandable lateral bone plate assemblies, and different configurations of expandable lateral bone plate assemblies so long as each expandable lateral bone plate assembly can stabilize adjacent bone structures. FIG. 11 illustrates an expandable lateral bone plate assembly 60 implanted on the lateral spinal region 61. in an expanded position.

Figure 12A:
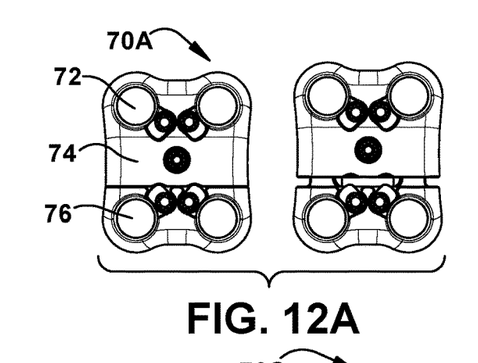
FIGS. 12A-12C are front views of a kit including expandable anterior lumbar and/or anterior sacrum bone plate assemblies according to an embodiment of the present invention illustrating such assemblies in a non-expanded position and a fully expanded position.
Figure 12B:
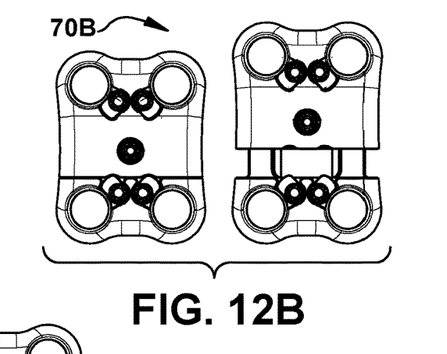
Figure 12C:
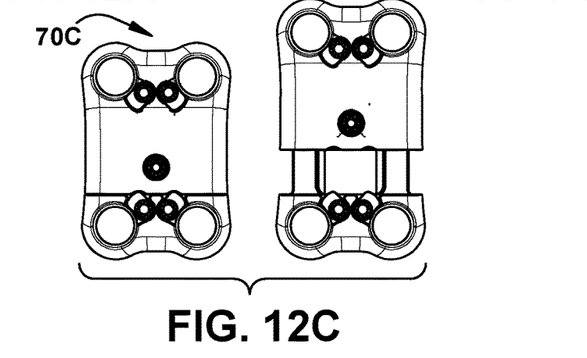
Figure 13:
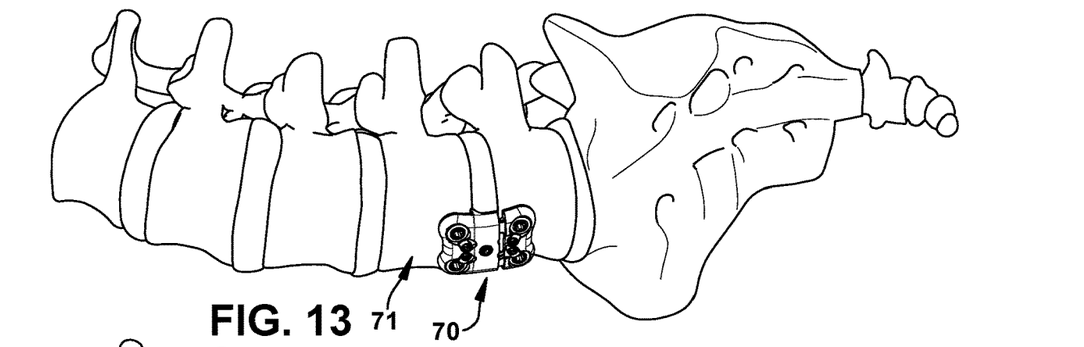
FIG. 13 is a perspective view of an expandable anterior lumbar bone plate assembly implanted on an anterior lumbar spinal region.
Figure 14:
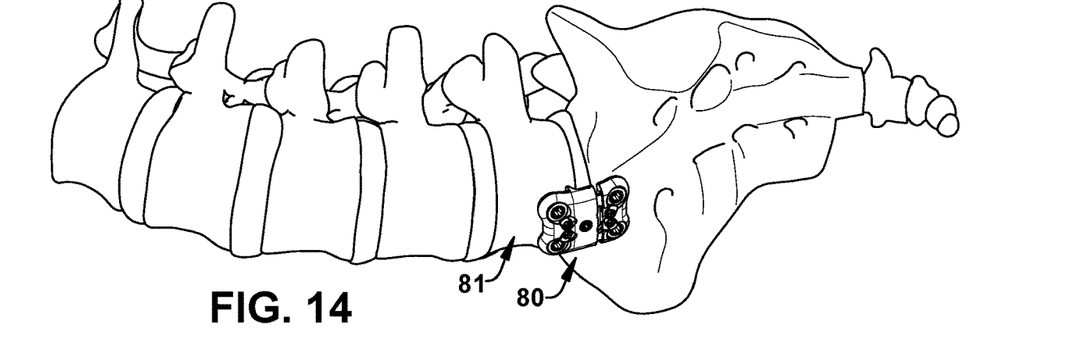
FIG. 14 is a perspective view of an expandable anterior sacrum bone plate assembly implanted on an anterior sacrum spinal region.

Referring to FIGS. 12A-12C, kit 50 can additionally or alternatively include three expandable anterior lumbar bone plate assemblies 70 ranging in size from approximately 23 millimeters (mm) to approximately 35 mm in a fully expanded position as measured from the center of the left screw hole 72 of top plate portion 74 to the center of left screw hole 76 of bottom plate portion 78. For example, expandable anterior lumbar bone plate assembly 70A as schematically illustrated in FIG. 12A can range in height from approximately 21 mm in a non-expanded position to approximately 23 mm in a fully expanded position. Expandable anterior lumbar bone plate assembly 70B as schematically illustrated in FIG. 12B can range in height from approximately 23 mm in a non-expanded position to approximately 27 mm in a fully expanded position. Expandable anterior lumbar bone plate assembly 70C as schematically illustrated in FIG. 12C can range in height from approximately 27 mm in a non-expanded position to approximately 35 mm in a fully expanded position. In certain embodiments, each expandable anterior lumbar bone plate assembly 70 includes four bone screw holes, four bone screw locks, is approximately 5 mm thick and is approximately 28 mm wide. In certain embodiments, kit 50 includes plate portions having plate positioning flanges as described in more detail below. Kit 50 can include different quantities of components of an expandable anterior lumbar bone plate assembly, different quantities of expandable anterior lumbar bone plate assemblies, and different configurations of expandable anterior lumbar bone plate assemblies so long as each expandable anterior lumbar bone plate assembly can stabilize adjacent bone structures. FIG. 13 illustrates an expandable anterior lumbar bone plate assembly 70 implanted on the anterior lumbar spinal region 71 in an expanded position. Anterior lumbar bone plate assemblies can be used, for example, for L1-L5 vertebrae. Kit 50 can additionally or alternatively include expandable anterior sacrum bone plate assemblies that have similar configurations to expandable anterior lumbar bone plate assemblies. FIG. 14 illustrates an expandable anterior sacrum bone plate assembly 80 implanted on the anterior sacral spinal region 81 in an expanded position. Anterior sacrum bone plate assemblies can be used, for example, for L5-S1 vertebrae.

Any of the kits described above can include bone screws and installation tools.

Figure 15A:
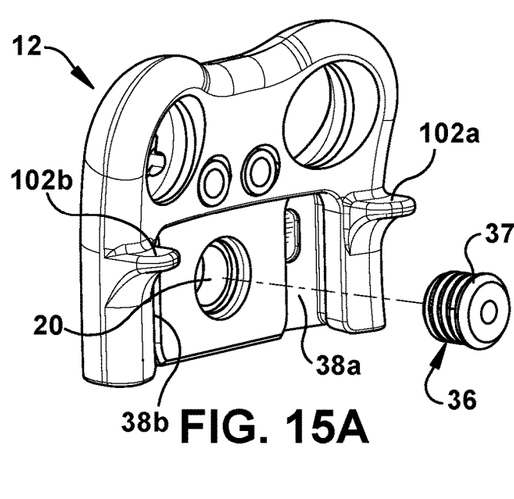
FIGS. 15A and 15B are perspective views of a top plate portion of an expandable bone plate assembly during one stage of manufacturing according to an embodiment of the present disclosure.
Figure 15B:
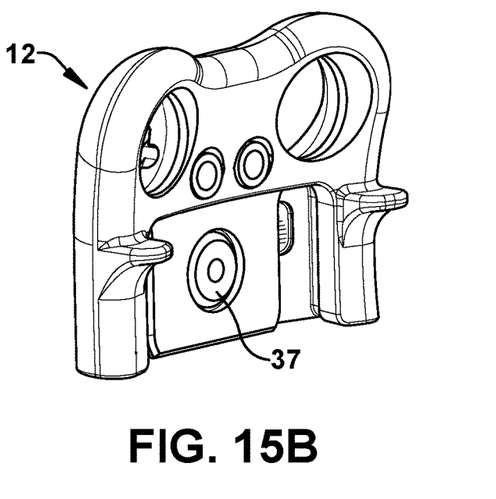
Figure 16A:
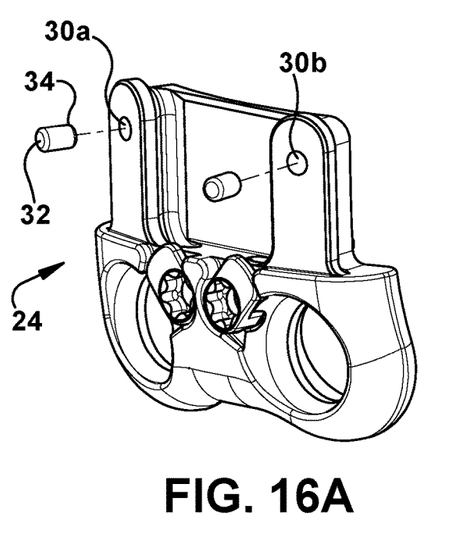
FIGS. 16A and 16B are perspective views of a bottom plate portion of an expandable bone plate assembly during another stage of manufacturing according to an embodiment of the present disclosure.
Figure 16B:
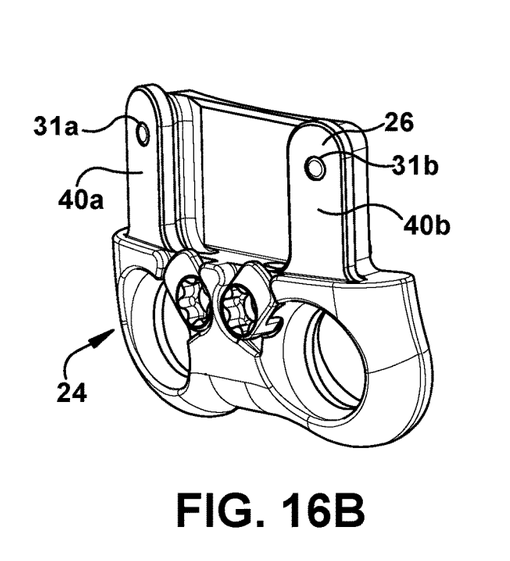
Figure 17:
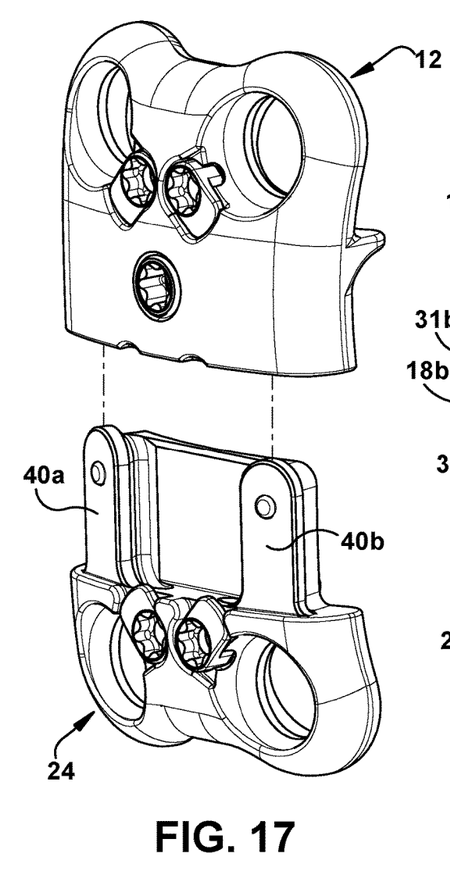
FIG. 17 is a perspective view of a top plate portion and a bottom plate portion of an expandable bone plate assembly during another stage of manufacturing according to an embodiment of the present disclosure.

FIGS. 15-17 illustrate different configurations of components of an expandable bone plate assembly at different stages of an exemplary manufacturing process. Referring to FIG. 15A, lock screw 36 is inserted into transversely extending counterbore 20 of top plate portion 12 until the lock screw head 37 bottoms on the counterbore's flat surface as schematically depicted in FIG. 15B. Referring to FIG. 16A, left pin 31a is inserted into left transversely extending bore 30a of bottom plate portion 24 and right pin 31b is inserted into right transversely extending bore 30b of bottom plate portion 24. The pins are inserted into the respective bores until the back of the pin shafts are flush with the immediately adjacent portions of front side 26 (such as longitudinally extending tabs 40a and 40b of bottom plate portion 24) as schematically illustrated in FIG. 16B. As indicated above, the outer diameter of the pin shaft is greater than the minor diameter of the transversely extending bore thereby creating an interference fit to retain the pin axially. Referring to FIG. 17, top plate portion 12 and bottom plate portion 24 are slide together. For example, left longitudinally extending tab 40a of bottom plate portion 24 can be inserted into left longitudinally extending groove 38a of top plate portion 12 and right longitudinally extending tab 40b of bottom plate portion 24 can be inserted into right longitudinally extending groove 38b of top plate portion 12. Referring to FIG. 18, the pins are pressed into their respective transversely extending bores until the pin heads 32 are bottomed into the longitudinally extending blind slots 18 of back side 16 of top plate portion 12. This prevent over-expansion of the bone plate assembly 10 as the bone plate portions can only be expanded the length of longitudinally extending blind slot 18 which does not extend through top and bottom ends of the back side of the top plate portion. FIG. 18 illustrates only right pin 31b bottomed into right longitudinally extending blind slot 18b for the sake of clarity but left pin 31a can similarly be bottomed into left longitudinally extending blind slot 18a. Pin 31b and optionally pin 31a retain expandable bone plate assembly 10 together so that the pins and lock screws are secured in the expandable bone plate assembly after manufacturing so that the components of the expandable bone plate assembly do not migrate out during transit (e.g. after manufacturing) and during and after implantation.

Figure 19:
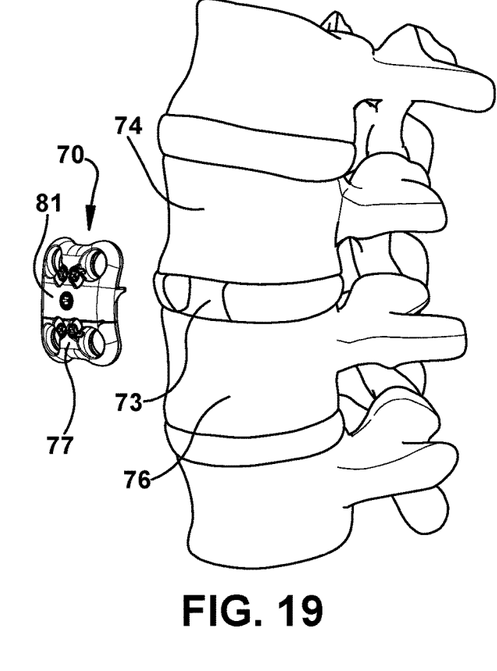
FIGS. 19 to 26 are perspective views illustrating an expandable bone plate assembly during various implantation steps during an anterior lumbar interbody fusion procedure according to an embodiment of the present disclosure.
Figure 20:
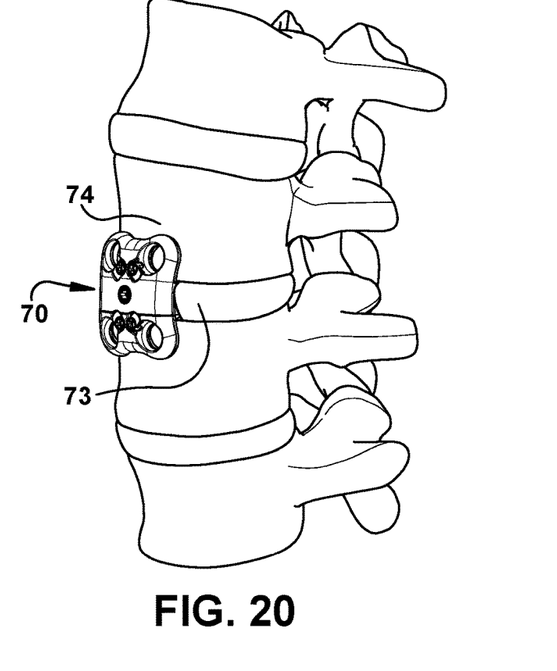
Figure 21:
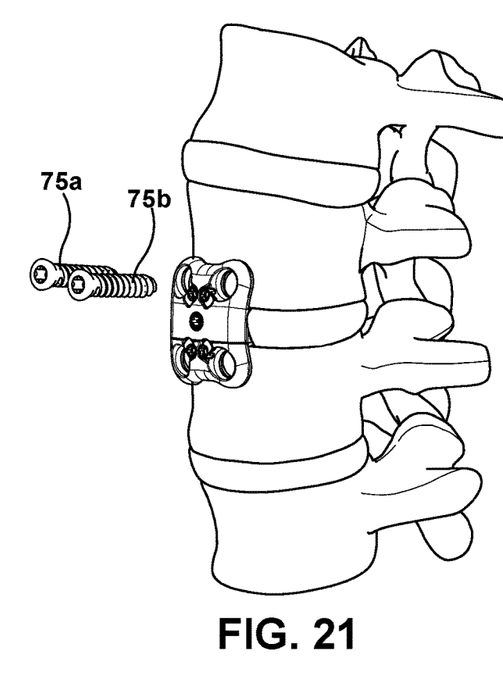
Figure 22:
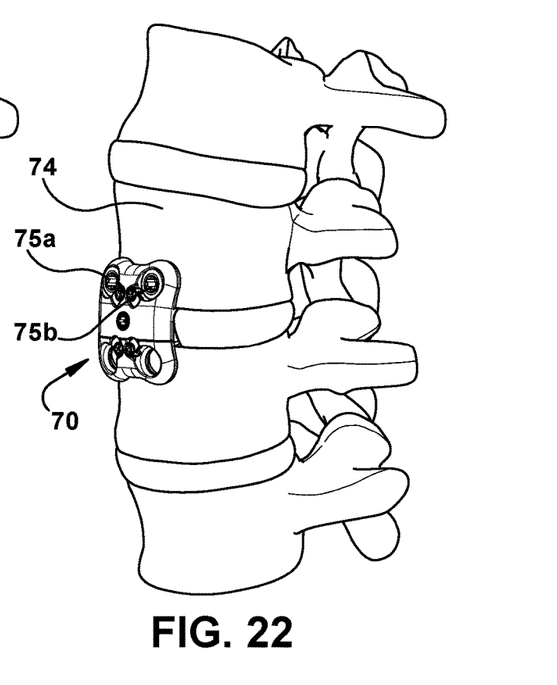
Figure 23:
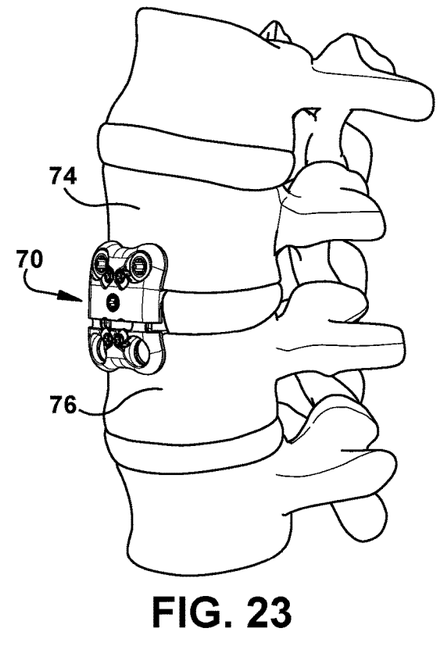
Figure 24:
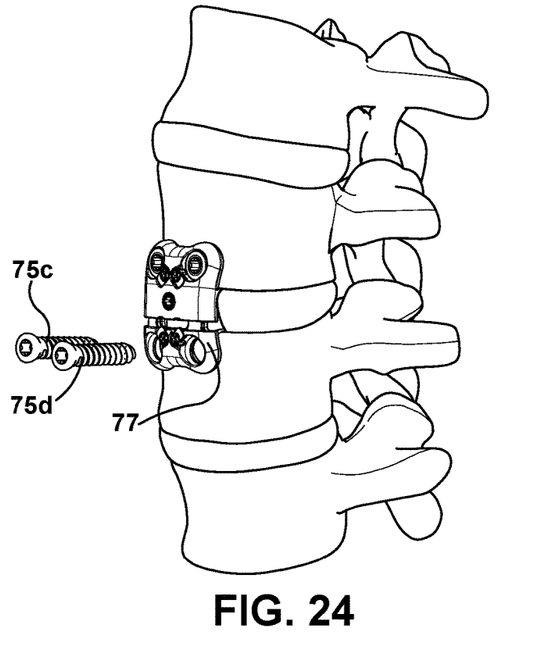
Figure 25:
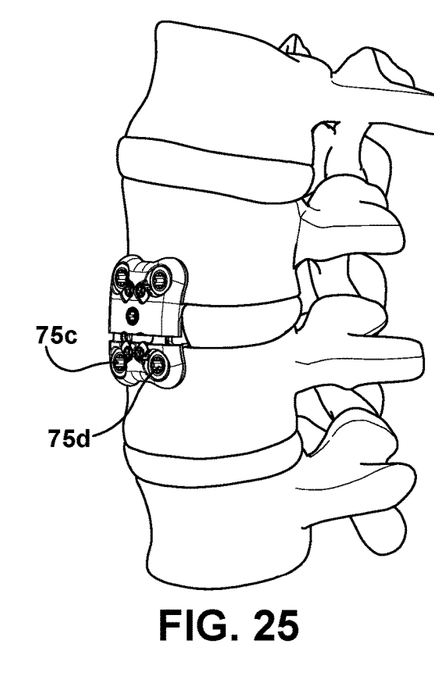
Figure 26:
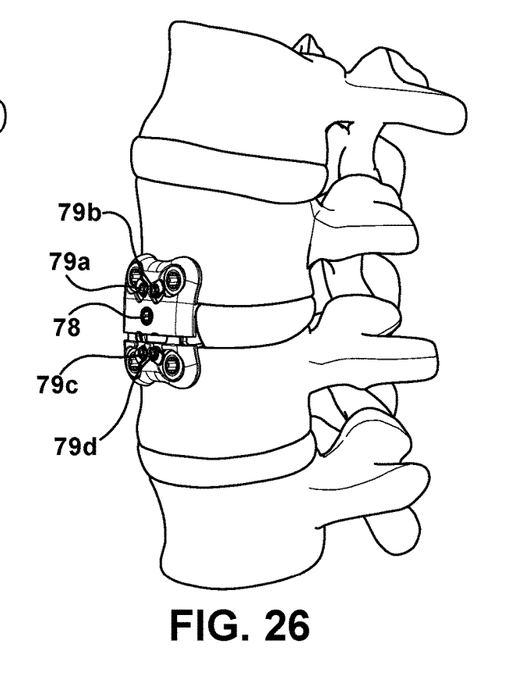

FIGS. 19 to 26 illustrate an exemplary method of implanting an expandable bone plate assembly for an anterior lumbar interbody fusion procedure. With reference to FIG. 19, a proper size of expandable plate assembly 70 selected to fit the prepared disk height. As illustrated in FIG. 20, bone plate assembly 70 is positioned in the disc space 73 while contacting the end plate 74 of one of the two adjacent vertebra. The proper bone screw type, size and length is selected to fit the patient's anatomy as depicted in FIG. 21. As illustrated in FIG. 22, the bone screws 75 are inserted into top plate portion 81 to retain the expandable bone plate assembly 70 to the vertebra 74 contacted in the second step described above as depicted in FIG. 20. The expandable bone plate assembly is expanded until contact is made with the opposite vertebra 76 as illustrated in FIG. 23. The proper bone screw type, size and length is selected to fit the patient anatomy as illustrated in FIG. 24. The remaining two bone screws 75 are inserted into the bottom plate portion 77 as shown in FIG. 25. Lock screw 78 is tightened to lock the expanded bone plate assembly into position and the four bone screw locks 79 are rotated to prevent migration of the bone screws 75 as depicted in FIG. 26.

Figure 27:
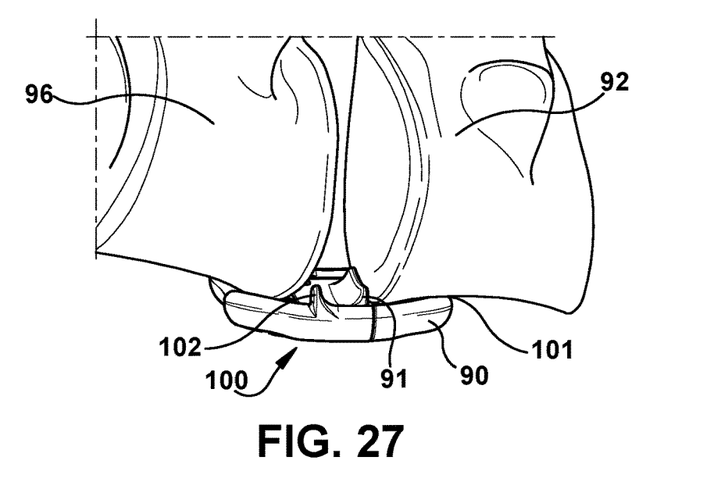
FIGS. 27-32 are perspective views illustrating an expandable bone assembly with plate positioning flanges during various implantation steps on a proximal and distal vertebra according to an embodiment of the present disclosure.
Figure 28:
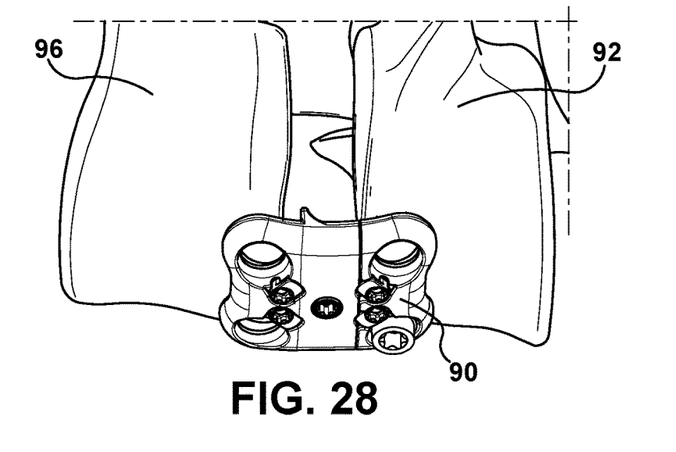
Figure 29:
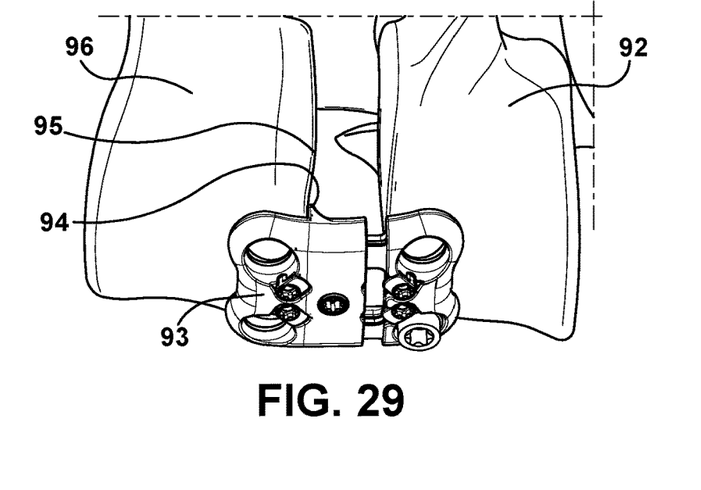
Figure 30:
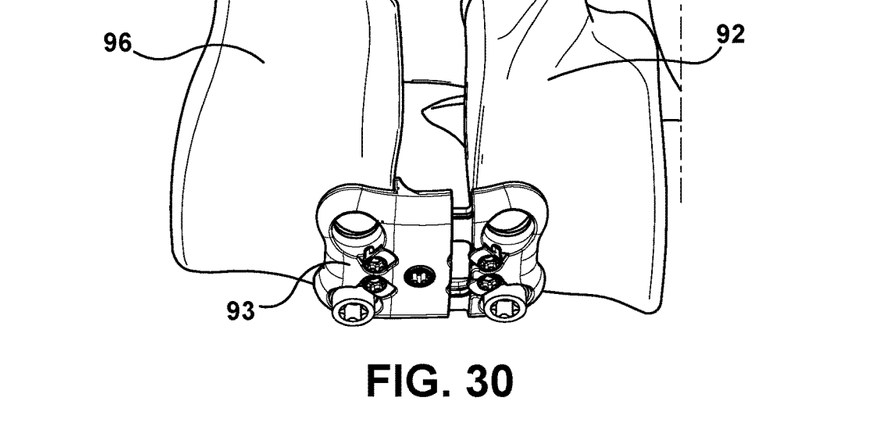
Figure 31:
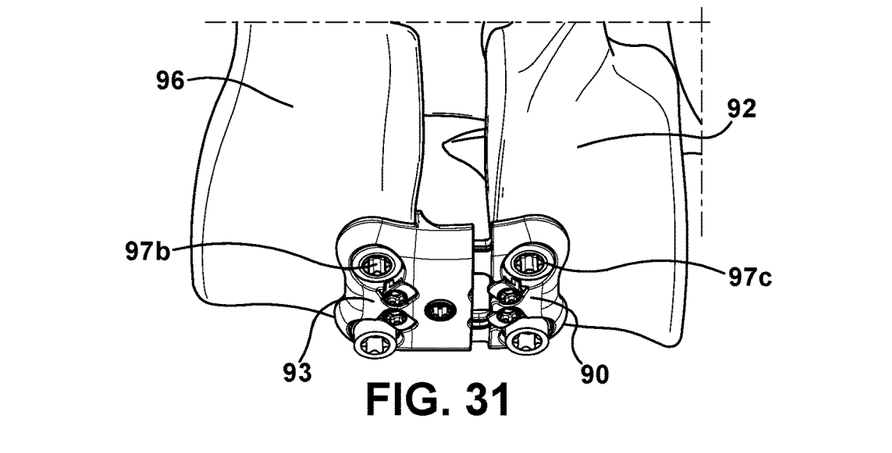
Figure 32:
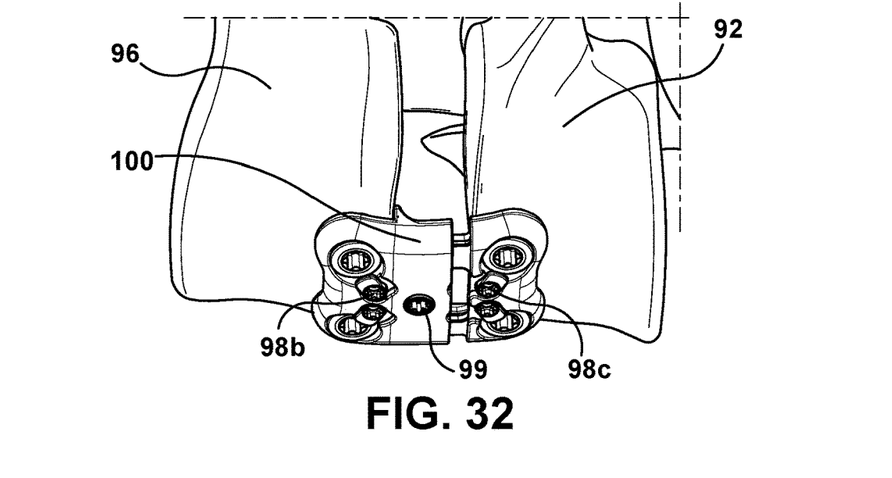

As stated above, in certain embodiments, a bone plate assembly includes positioning flanges extending from the back sides of top plate portion and the bottom plate portion of a bone plate assembly as depicted in FIGS. 2 and 3. With reference to FIG. 27 the positioning flange 91 of bottom plate portion 90 is positioned against the anterior rim 101 of the distal vertebral body 92. Bottom plate portion 90 is temporarily attached to distal vertebral body 92 as illustrated in FIG. 28. Referring to FIG. 29, top plate portion 93 is expanded until positioning flange 94 rests against the anterior rim 95 of the proximal vertebral body 96. Top plate portion 93 is temporarily attached to proximal vertebral body 96 as depicted in FIG. 30. Referring to FIG. 31, bone screws 97 are installed into top and bottom plate portions 93 and 90. Referring to FIG. 32, bone screw locks 98 are rotated to cover a portion of the bone screws 97 of top and bottom plate portions 93 and 90. The expandable bone plate assembly 100 is locked by applying torque (via a torque limiting handle, for example) to the lock screw 99 to tighten lock screw 99.

Expandable bone plate assemblies as disclosed herein can be used for bone fractures, bone fusion, and other medical procedures requiring fixation of tissue. Such devices can be configured to be implanted on the spinal column, such as, for example, the cervical spinal region, the lumbar spinal region or the sacral spinal region. The devices also can be configured as occipito-cervico-thoracic fixation devices to treat pathologies of the occipitocervical junction, and the posterior cervical and upper thoracic spine. Alternatively, bone plate assemblies can be configured to stabilize skull fractures, facial fractures, or craniomaxillofacial fractures. The bone plate assemblies can be left in place in the patient or removed after the bone has fused.

In certain embodiments, a bone plate assembly can be used as a supplemental fixation device and can be part of a kit of bone plates assemblies of a variety of shapes and sizes of one-level lumbar and sacral plates assemblies and screws. Bone plate assemblies can attach to the lumbar and lumbosacral spine (L1-S1). Bone plate assemblies can be implanted via a lateral or anterolateral surgical approach above the bifurcation of the great vessels in the treatment of the lumbar spine (L1-L5) or via an anterior approach below the bifurcation of the great vessels in the treatment of the lumbar and the lumbosacral spine (L1-S1). A bone plate assembly can provide immobilization and stabilization as an adjunct to fusion in skeletally mature patients in the treatment of, for example, fracture (including dislocation and subluxation); tumor; degenerative disc disease (defined as back pain of discogenic origin with degeneration of the disc confirmed by patient history and radiographic studies); pseudoarthrosis; spondylolysis; spondylolisthesis; scoliosis; lordotic deformities of the spine; spinal stenosis; and/or failed previous spine surgery Each of the disclosed aspects and embodiments of the present disclosure may be considered individually or in combination with other aspects, embodiments, and variations of the disclosure. Further, while certain features of embodiments of the present disclosure may be shown in only certain figures, such features can be incorporated into other embodiments shown in other figures. Unless otherwise specified, none of the steps of the methods of the present disclosure are confined to any particular order of performance.

What is claimed is:

1. An expandable bone plate assembly comprising:
   a top plate portion comprising a front side, a back side comprising a longitudinally extending blind slot, a transversely extending counterbore extending through the front and back sides of the top plate portion, and a bone screw hole extending through the front and back sides of the top plate portion;
   a bottom plate portion comprising a front side, a back side, a transversely extending bore extending through the front and back sides of the bottom plate portion and a bone screw hole extending through the front and back sides of the bottom plate portion;
   a pin comprising a pin head and a pin shaft depending from the pin head, the pin shaft disposed within the transversely extending bore of the bottom plate portion and having an outer diameter greater than the minor diameter of the transversely extending bore, the pin head disposed against the longitudinally extending blind slot of the top plate portion; and
   a lock screw disposed within the transversely extending counterbore of the top plate portion.

2. The expandable bone plate assembly of claim 1, wherein the transversely extending bore of the bottom plate portion is a counterbore and the pin head comprises a flange, the flange disposed against the longitudinally extending blind slot of the top plate portion.

3. The expandable bone plate assembly of claim 1, wherein the bone screw hole of the top plate portion comprises at least two bone screw holes.

4. The expandable bone plate assembly of claim 1, wherein the bone screw hole of the bottom plate portion comprises at least two bone screw holes.

5. The expandable bone plate assembly of claim 1, wherein the longitudinally extending blind slot of the top plate portion comprises a left longitudinally extending blind slot and a right longitudinally extending blind slot.

6. The expandable bone plate assembly of claim 5, wherein the transversely extending bore of the bottom plate portion comprises a left transversely extending bore and a right transversely extending bore.

7. The expandable bone plate assembly of claim 6, wherein the pin comprises:
   a left pin comprising a left pin head and a left pin shaft depending from the left pin head flange, the left pin shaft disposed within the bottom plate's left transversely extending bore and having an outer diameter greater than the minor diameter of the left transversely extending bore, the left pin head disposed against the left longitudinally extending blind slot of the top plate portion; and
   a right pin comprising a right pin head and a right pin shaft depending from the right pin head, the right pin shaft disposed within the bottom plate's right transversely extending bore and having an outer diameter greater than the minor diameter of the right transversely extending bore, the right pin head disposed against the right longitudinally extending blind slot of the top plate portion.

8. The expandable bone plate assembly of claim 1, wherein the front side of the bottom plate portion comprises a left and a right longitudinally extending tab that is disposed in a respective left and right longitudinally extending groove of the back side of the top plate portion.

9. The expandable bone plate assembly of claim 1, further comprising a recess in fluid communication with the bone screw hole of the top plate portion; and
   a rotatable bone screw lock mounted in the recess of the top plate portion and having a lock head including a laterally extending flange, wherein in a locked position, a part of the laterally extending flange is within the bone screw hole of the top plate portion.

10. The expandable bone plate assembly of claim 1, wherein a recess is in fluid communication with the bone screw hole of the top plate portion, the recess defined by a retention portion of the front side of the top plate portion, a lower surface of the top plate portion, and a discontinuous wall comprising a gap in fluid communication with the bone screw hole of the top plate portion; and
   a rotatable bone screw lock mounted in the recess of the top plate portion and having a lock head including a laterally extending flange having an outer edge that is below the front side of the top plate portion, wherein in a locked position, a part of the laterally extending flange is within the gap, and another part of the lock head is covered by the retention portion of the front side of the top plate portion.

11. The expandable bone plate assembly of claim 1, further comprising a recess in fluid communication with the bone screw hole of the bottom plate portion; and
   a rotatable bone screw lock mounted in the recess of the bottom plate portion and having a lock head including a laterally extending flange, wherein in a locked position, a part of the laterally extending flange is within the bone screw hole of the bottom plate portion.

12. The expandable bone plate assembly of claim 1, wherein a recess is in fluid communication with the bone screw hole of the bottom plate portion, the recess defined by a retention portion of the front side of the bottom plate portion, a lower surface of the bottom plate portion, and a discontinuous wall comprising a gap in fluid communication with the bone screw hole of the bottom plate portion; and
   a rotatable bone screw lock mounted in the recess of the bottom plate portion and having a lock head including a laterally extending flange having an outer edge that is below the front side of the bottom plate portion, wherein in a locked position, a part of the laterally extending flange is within the gap, and another part of the lock head is covered by the retention portion of the front side of the bottom plate portion.

* * * * *